United States Patent
Price

Patent Number: 5,230,330
Date of Patent: Jul. 27, 1993

[54] RESUSCITATION AND INHALATION DEVICE

[76] Inventor: William E. Price, 3704 St. Clair Ave. E., Scarborough, Ontario, M1M 1T2, Canada

[21] Appl. No.: 656,504

[22] Filed: Feb. 19, 1991

[30] Foreign Application Priority Data

Mar. 6, 1990 [CA] Canada ............................... 2011609

[51] Int. Cl.⁵ .............................................. A61M 16/00
[52] U.S. Cl. ............................... 128/203.11; 128/205.24
[58] Field of Search ................... 128/203.11, 204.18, 128/204.19, 205.24, 205.25

[56] References Cited

U.S. PATENT DOCUMENTS

| | | | |
|---|---|---|---|
| 402,779 | 6/1889 | Steinhoff | 128/30.2 |
| 2,273,790 | 2/1942 | Raymond | 128/204.19 |
| 2,364,626 | 12/1944 | Emerson | 128/204.25 |
| 3,039,481 | 6/1962 | Schreiber et al. | 128/204.19 |
| 3,209,748 | 10/1965 | Thomas | 128/53 |
| 3,279,487 | 10/1966 | Elam | 137/505.12 |
| 3,333,581 | 8/1967 | Robinson | 128/30.2 |
| 3,509,899 | 6/1970 | Hewson | 128/204.18 |
| 3,581,742 | 6/1971 | Glenn | 128/204.19 |
| 3,610,237 | 10/1971 | Bar et al. | 128/204.19 |
| 4,210,174 | 7/1980 | Eross | 137/528 |
| 4,297,999 | 11/1981 | Kitrell | 128/205.16 |
| 4,349,015 | 9/1982 | Alferness | 128/28 |
| 4,606,339 | 8/1986 | Walther | 128/204.19 |
| 4,664,355 | 6/1987 | Kubach | 251/65 |
| 4,796,619 | 1/1989 | Walther | 128/204.19 |
| 4,825,904 | 6/1989 | Grau et al. | 137/554 |

FOREIGN PATENT DOCUMENTS

| | | | |
|---|---|---|---|
| 887445 | 12/1971 | Canada | 128/204.19 |
| 1163132 | 9/1969 | United Kingdom | 128/204.19 |

*Primary Examiner*—Edgar S. Burr
*Assistant Examiner*—Aaron J. Lewis
*Attorney, Agent, or Firm*—McFadden, Fincham, Marcus & Anissimoff

[57] ABSTRACT

A resuscitation and inhalation device which can be used alternatively in each of two modes. The flow of oxygen or gas is controlled by a control valve, itself controlled by a movable member acted upon by the pressure of oxygen or gas in a chamber after having flowed past the control valve. On meeting a preset maximum pressure, the valve member moves to close the control valve. The movable valve member is acted upon by a magnetic field which is adjustable, and the magnetic field strength sets the pressure at which the valve member moves. Oxygen or gas is admitted to the control valve by two alternative inlet valves, one for resuscitation with only oxygen or gas flowing through the mask, and one for inhalation, with a mixture of oxygen or gas and air or a second gas being fed through the mask.

11 Claims, 4 Drawing Sheets

RESUSCITATION AND INHALATION DEVICE

FIELD OF THE INVENTION

This invention relates to a flow control valve device.

BACKGROUND OF THE INVENTION

More particularly, one aspect of this invention relates to a flow control valve for use in devices for controlling a source of fluid. Inasmuch as the present invention has particular application as a flow control valve for equipment such as inhalation devices, particular reference will be made to such devices in describing the present invention, although it is understood that the flow control valve may be used for various purposes, such as those described hereinafter.

Masks for resuscitation, where oxygen or gas is fed to a person for breathing and for inhalation, are known where a mixture of oxygen or gas and air or other gas is fed to a person, or primarily used by non-medical personnel, such as fire-fighters, police and ambulance personnel. Information concerning the person being treated is usually not available. Therefore, great care and attention is required to prevent a mishap from occurring, particularly in relation to the person being treated. The oxygen or gas, which is applied to the lungs of the person, is usually supplied in containers of a relatively high pressure.

SUMMARY OF THE INVENTION

The present invention provides a resuscitation and inhalation device, suitable for manual operation by a non-medical person. Safeguards are provided to ensure that safe maximum pressures will not be exceeded. Oxygen or gas under pressure enters on operation of an inlet valve, the oxygen or gas flowing past a first open valve into a chamber. The oxygen or gas in the chamber acts on a movable valve member which, when the oxygen or gas pressure in the chamber reaches a safe, preset maximum pressure, moves against a magnetic field, permitting the first valve to close. Oxygen or gas flows from the chamber through connections to a face mask. The lungs are inflated at this time and then the patient starts to exhale. The patient's breath passes the movable valve member to escape. On conclusion of the exhaling step, the movable valve member moves under light spring pressure to open the first valve. The initial pressure of the movable valve member is set by the strength of the magnetic field experienced by the movable valve member, and this can be adjusted. Breathing of oxygen or gas will continue as long as the inlet valve is held open, providing resuscitation.

For inhalation, where a mixture of oxygen or gas and air or a different gas is continuously supplied, and inhaled by the patient, a second valve is activated to allow a continuous feed of oxygen or gas. By connections, the oxygen or gas again flows past the first, open valve to the chamber. The same control of maximum oxygen or gas pressure occurs by the movable valve member. The oxygen or gas then flows to a mixing chamber, where it mixes with air or a different gas and then flows to the face mask.

In the prior art, there are numerous references which describe flow control valves. For example, reference may be made to the following United States patents, namely, U.S. Pat. No. 3,039,481—Schreiber et al. (1962);
U.S. Pat. No. 3,209,748—Thomas (1965);
U.S. Pat. No. 4,606,339—Walther (1986);
U.S. Pat. No. 4,664,355—Kubach (1987);
U.S. Pat. No. 4,796,619—Walther (1989);
U.S. Pat. No. 4,825,904—Grau et al. (1989);
U.S. Pat. No. 402,779—Steinhoff (1889);
U.S. Pat. No. 2,364,626—Emerson (1944);
U.S. Pat. No. 3,279,487—Elam (1966);
U.S. Pat. No. 3,333,581—Robinson et al. (1967);
U.S. Pat. No. 3,509,899—Hewson (1970);
U.S. Pat. No. 3,610,237—Barkalow et al. (1971);
U.S. Pat. No. 4,297,999—Kitrell (1981); and
U.S. Pat. No. 4,349,015—Alferness (1982).

The above references teach valves which generally tend to include very complex components or alternatively, have limited application due to their structural features. Certain of these references do disclose the use of magnetic valves, e.g., U.S. Pat. No. 4,664,355—Kubach (1987), as well as U.S. Pat. No. 4,796,619—Walther (1989), the latter of which permits sourcing of a single incoming gaseous fluid.

There is a need for a relatively simple, reliable and economical device which can be used in different functional modes, and to this end, one aspect of the present invention includes the feature that energy required to change the valve states is derived from the magnetic property of the valve with minor assist using a component associated with the magnetic valve, and operating in conjunction with the pressures in a variable pressure system.

According to one aspect of this invention, there is thus provided a flow control valve apparatus, comprising a chamber; a valve member reciprocally mounted in the chamber; a flow control valve, acted upon by the valve member to an open position; means for connecting a high pressure source to an inlet of the valve; means for connecting a variable pressure volume to the chamber; means for selectively connecting a low pressure volume to the chamber; a first magnetic member on the valve member; a second magnetic member in spaced opposition to the first magnetic member; one of the first and second magnetic members being magnetized, to restrain movement of the valve member; the valve member being moved against the restrain when the variable pressure reaches a predetermined maximum value, to permit closing of the flow control valve, and to permit the connection of the low pressure volume to the chamber; and the valve member being moved with the restrain when the variable pressure reaches a predetermined low value, to open the flow control valve.

According to another aspect of the invention, there is also provided a resuscitation and inhalation device comprising a gaseous flow control valve to control flow of a gas to a chamber; a movable valve member, acted upon by the pressure of gas in the chamber, the movable valve member including a magnetic member, the movable valve member being biased to act on the gaseous flow control valve to move it to an open position; a magnetic member being in the chamber; one of the magnetic members being magnetized, the magnetic field of the magnetized member acting upon the other magnetic member to restrain movement of the movable valve member; alternate first and second gaseous inlet valves for admitting a first gas under pressure to the gaseous flow control valve; operation of a first of the alternate inlet valves permitting flow only when manually held in an actuated position; operation of a second of the alternative inlet valves permitting continuous flow of gas to the gaseous flow control valve; gaseous access means for admitting a second gas to a mixing chamber; and seating means associated with the first alternate inlet valve for closing the gaseous access means on operation of the first inlet valve, whereby on operation of the first inlet valve, the first gas can flow to a connector for flow to a mask, and on operation of the second alternate inlet valve, the first gas is mixed with the second gas in the mixing chamber prior to flowing to the connector and to the mask.

According to another aspect of the present invention, there is also provided, broadly, a resuscitation and inhalation device comprising a first gaseous flow control valve, a movable valve member acted upon by the pressure of the first gas in a chamber, the movable valve member acting against an adjustable magnetic field, and alternate gaseous inlet valves for permitting flow of the first gas to the first gaseous flow control valve, operation of a first of the inlet valves permitting flow only when held in an actuated position and also, cutting off flow of a second gas to a mixing chamber in the device, operation of a second of the inlet valves permitting continuous flow of the first gas to the first gaseous flow control valve.

In preferred embodiments of the above apparatus, the device has a variable magnetic distance—thus, the distance between the magnetic members is variable. Still further, the device preferably includes a housing, an annular seating member in the housing, the movable valve member being positioned in the annular seating member and seatable on a seat in the seating member, and with the seating member being movable to vary the distance between the magnetic members.

According to another preferred aspect of the invention, the device includes an external sleeve on the housing and a screw thread between the sleeve and the housing, and means connecting the sleeve to the seating member, whereby rotation of the sleeve on the housing varies the distance between the magnetic members.

According to a further preferred aspect of the invention, the device includes an annular magnet in the housing, aligned with and spaced from the movable valve member, and having a flow control valve mounted for axial movement in the annular magnet.

According to a still further preferred structure, the device has a first oxygen or gaseous inlet valve which includes an operating member, and the operating member comprises mounting means, e.g., a button, slidable axially in a valve seating member, the first inlet valve comprising a ball valve and the mounting means or button including an extension for lifting the ball valve off its seating on movement of the button, and biasing means biasing the button to a non-operative position. In this structure, preferably the second inlet valve comprises a needle-valve.

According to a preferred aspect of the above structure, the device has a gaseous flow control valve which includes a stem and a head, the movable valve member acting on an end of the stem, and the head forming a seating at an end remote from the movable valve member.

The above device preferably includes an inset or insert in the annular magnet, the stem being movable axially in the inset or insert, and flats on the stem extending the length thereof, for flow of a gas past the stem.

According to still another preferred aspect of the invention, the device includes an inlet for supply of the gas to the alternate first and second gaseous inlet valves, and a control valve is mounted on the inlet for controlling gas flow therethrough, the control valve including a first flow passage open at all times for a predetermined minimum gas flow, and a second, openable flow passage for additional flow of gas to a predetermined maximum.

The flow control device of the present invention can be housed in an appropriate housing of suitable material; for example, a housing of plastic or non-magnetic metallic material can be utilized. Preferably, and particularly when using the flow control valve of the present invention in a resuscitation and inhalation device, the housing will be substantially airtight and dustproof to prevent undesired particulate material from gaining access to the flow control valve.

In use in an inhalation device, the device of the present invention can be provided with appropriate connections to a source of gaseous fluid such as oxygen or any other desired gas; thus, the device of the present invention is adaptable to conventional masks through appropriate conduit connections.

In preferred embodiments, the magnetic member is permanently magnetized—i.e., a permanent magnet, although it will be understood that for various applications, an electromagnet can be utilized with appropriate current sources.

The device of the present invention permits adjustability of the gaseous flows, and comparing the device of the present invention to prior art devices which utilize springs for adjustment, the magnetic valve arrangement permits very specific and delicate adjustments when required. Thus, the device of the present invention will find use in various types of safety valves which require precise adjustments for exact control of gaseous flows.

A primary safety feature of the present invention is that the valve releases under conditions where comparable spring-type valves would maintain pressure. Still further, the valves of the present invention are position-independent, compared to prior art systems.

Other possible applications for the control valve of the present invention include use in clutch drives, permitting compensation for wear on a clutch plate, or in heat-activated systems where complete release under the operating environment is required.

Having thus generally described the invention, reference will now be made to the accompanying drawings, illustrating preferred embodiments and in which:

DETAILED DESCRIPTION OF THE PREFERRED EMBODIMENTS

Figure 1:
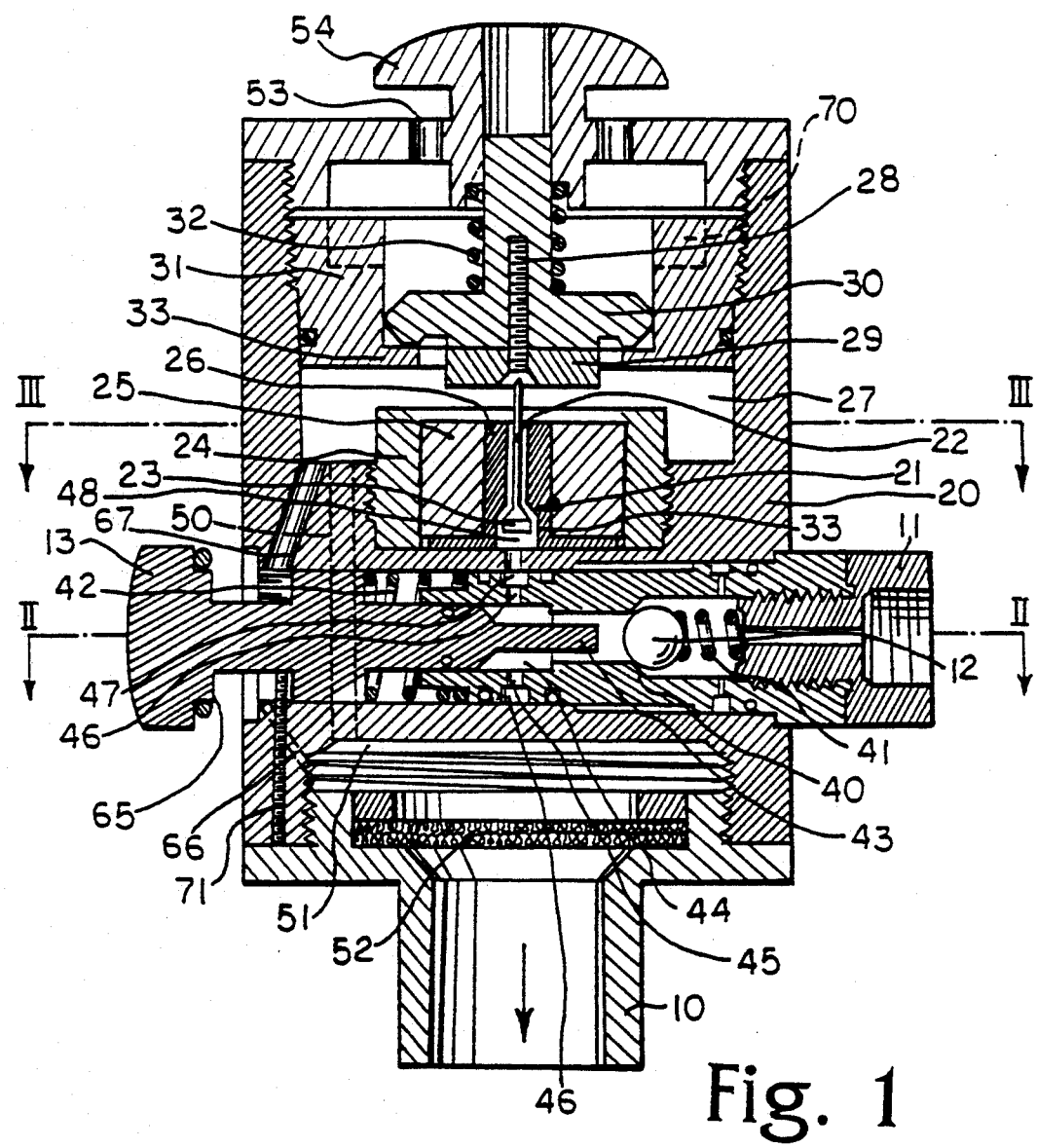
FIG. 1 is a vertical cross-section through a device of the present invention.
Figure 2:
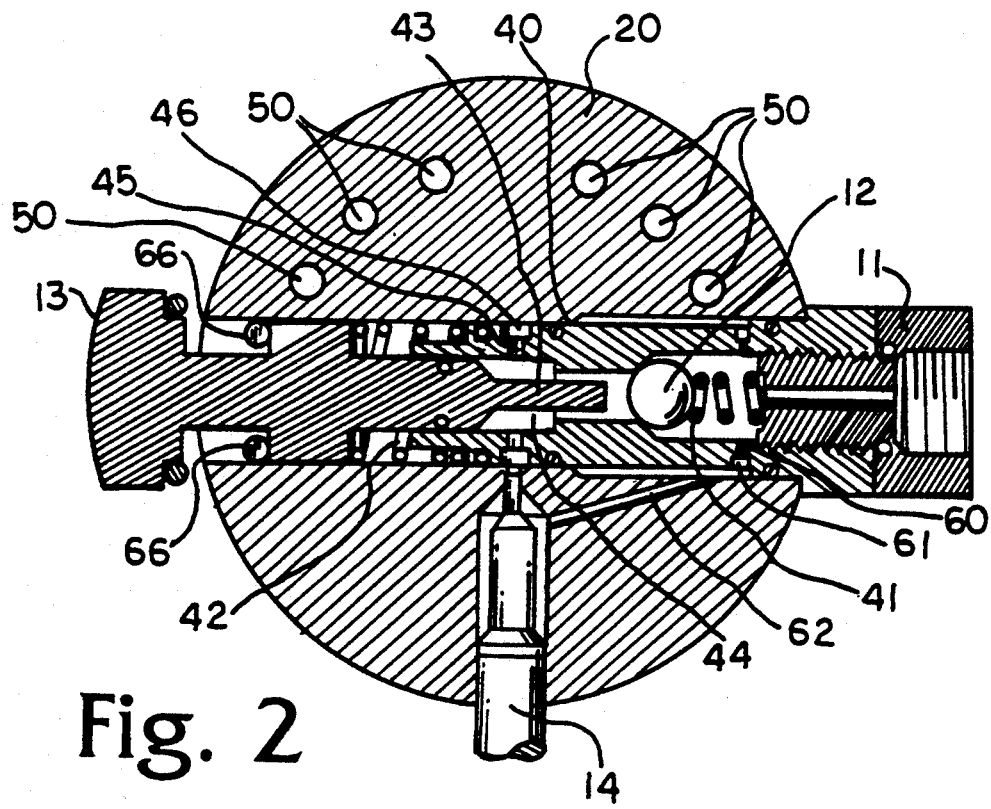
FIG. 2 is a cross-section on the line II—II of FIG. 1.
Figure 3:
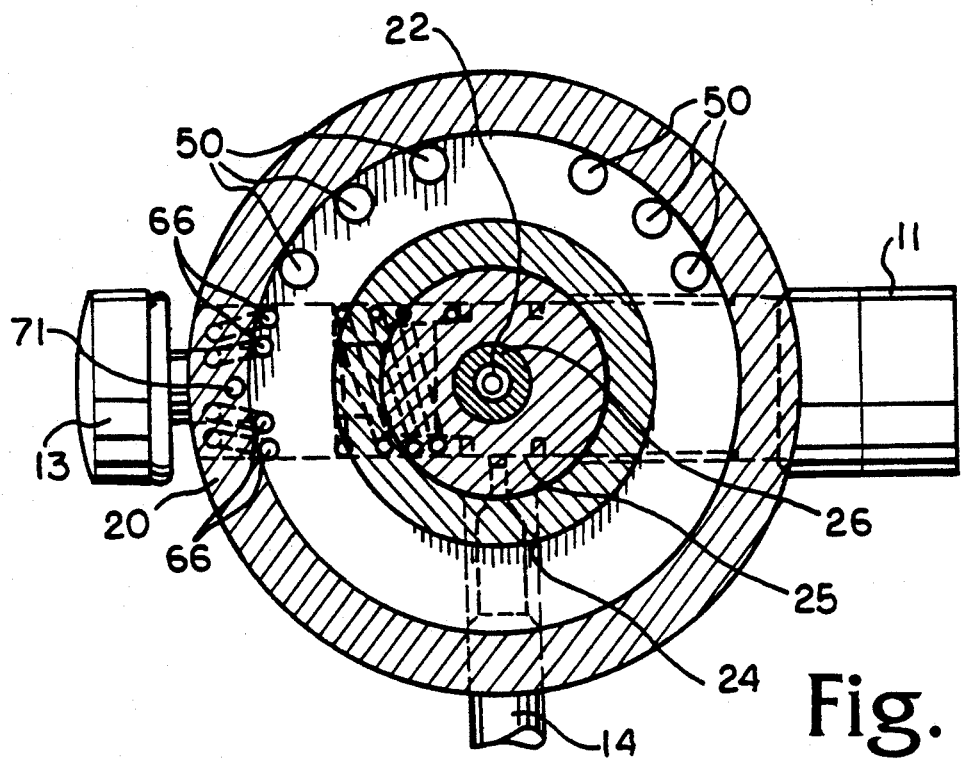
FIG. 3 is a cross-section on the line III—III of FIG. 1.

The apparatus, as illustrated in FIGS. 1, 2 and 3, is adapted to be mounted onto a conventional face mask (not shown), there being a connector 10 which connects by suitable means to the interior of the mask. Oxygen or gas is supplied to the apparatus at a connection 11. A first oxygen inlet valve 12, which may be a ball valve, is actuated by a button 13; and a second inlet valve 14, preferably in the form of a needle-type valve, can provide for a continuous flow of oxygen.

The apparatus comprises a main housing 20, in which is mounted an oxygen flow control valve 21, having a stem 22 and a head 23. In the example illustrated, the stem 22 has a somewhat triangular cross-section, with flats extending the length of the stem, so as to permit gaseous flow past the stem 22. A Teflon (trade mark) member 24 holds an annular magnetic member 25, the valve stem 22 moving in an insert, for example, a Teflon insert 26. The head 23 forms a seating member for the valve 21. Surrounding the member 24 is a chamber 27. Positioned in alignment with the valve 21 is a valve member 30, for example, of Teflon, with a magnetic metal member 29 attached thereto by a bolt 28. The valve member 30 moves in an adjustable seating member 31 which can be moved axially by rotation in the housing 20 to preset the distance between the magnetic metal member 29 and the magnetic member 25. A light spring 32 biases the valve member 30 down into contact with the seating 33 of the seating member 31. In an alternative arrangement, the bore of the insert 26 can have grooves extending along the bore, the stem 22 being cylindrical.

The button 13 slides in a valve seating member 40 in which seats the valve 12, the valve 12 being biased against the seating 40 by a spring 41. The button 13 is biased to an outward position by a spring 42. The button 13 is limited in its movement by the effect on spring 42 by pin 71.

Figure 4:
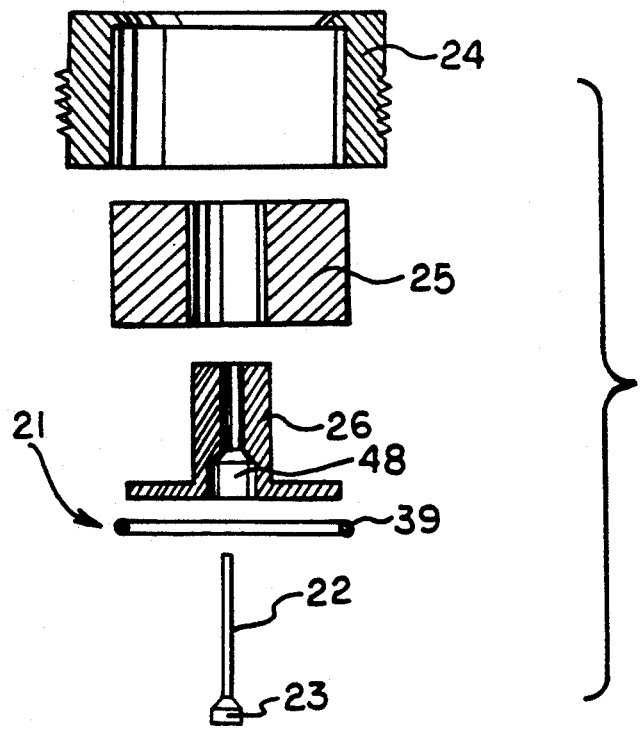
FIG. 4 is an exploded cross-sectional view of the oxygen control flow valve, magnetic member and insert, as illustrated in FIG. 1.

FIG. 3 illustrates the flow control valve 21 in more detail, showing the stem 22 and head 23, together with the annular magnetic member 25, insert 26 and the member 24, which holds the magnetic member 25 and insert 26 in position in the housing 20. Seen more clearly in FIG. 4 is an O-ring 39, which seals the insert 26 and magnetic member 25 against the housing 20.

For resuscitation, the button 13 is pushed in, with a stem 43 at the inner end lifting valve 12 off its seating 40. Oxygen flows through connection 11, past the valve 12, into chamber 44 and by passageway 45 and groove 46 and passageway 47 into the chamber 48 beneath the valve head 23 of the valve 21. With the valve 21 open, oxygen flows up past the stem 22 to the chamber 27. From the chamber 27, the oxygen flows through passageways 50, chamber 51, through filter 52 into the connector 10 and then to the face mask.

The oxygen in the chamber 27 acts on the lower end of the valve member 30, and when the pressure in the chamber 27 reaches the maximum desired pressure, the valve member 30 moves up and allows valve 21 to close. The valve 21 closes under the action of the flow of oxygen from passageway 47. This will represent the end of the inhalation step of the patient. The patient then exhales, via the chamber 51, passageways 50, chamber 27, past valve 30 via recesses 70, and out of vents 53, the air being deflected by deflector 54. When the patient stops exhaling, valve member 30 is returned by spring 32, valve 21 is open and the sequence restarts. The pressure at which the valve member will start to move will depend upon the magnetic effect of the magnet 25 on the magnetic metal member 29. This can be determined by varying the distance between magnet 25 and magnetic metal member 29, and this obtained by the adjustable seating member 31.

Figure 1A:
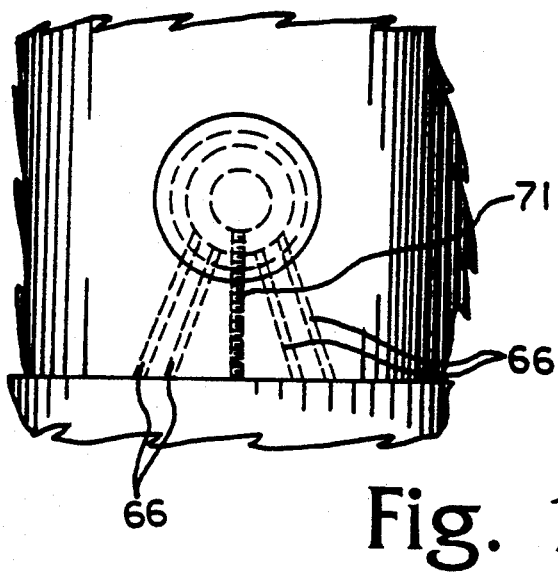
FIG. 1A is a partial side view, in the direction of the arrow A in FIG. 1, with the button head 13 omitted for clarity.

For inhalation, a controllable continuous flow of oxygen is provided by the valve 14. Oxygen flows from connector 11 through grooves 60 and 61, passageway 62, past the valve seating member 40 and into the groove 46 through passageway 47 to the chamber 48. It then flows up past valve 21, into chamber 27, and through passageways 50 to chamber 51. In the resuscitation mode, when the button 13 is pushed in, an annular seat 65 shuts off access to passageways 66, which otherwise permits air to enter chamber 51. In the inhalation mode, the button 13 is in an outer position, thus air flows into chamber 51 to mix with the oxygen and flow to the connector 10, and also flows into the chamber 27. The passageways 66 are seen more clearly in FIG. 1A and are also see in FIG. 3.

The valve member 30 acts in the same manner to control the maximum oxygen pressure in chamber 27. On reaching the desired maximum pressure, i.e., at the end of inhalation, the valve 30 moves, thereby closing valve 21. At the end of exhalation, the valve member 30 opens valve 21 for the sequence to resume. The exhaled breath passes through the chamber 51 and out the passageway 67.

Figure 5:
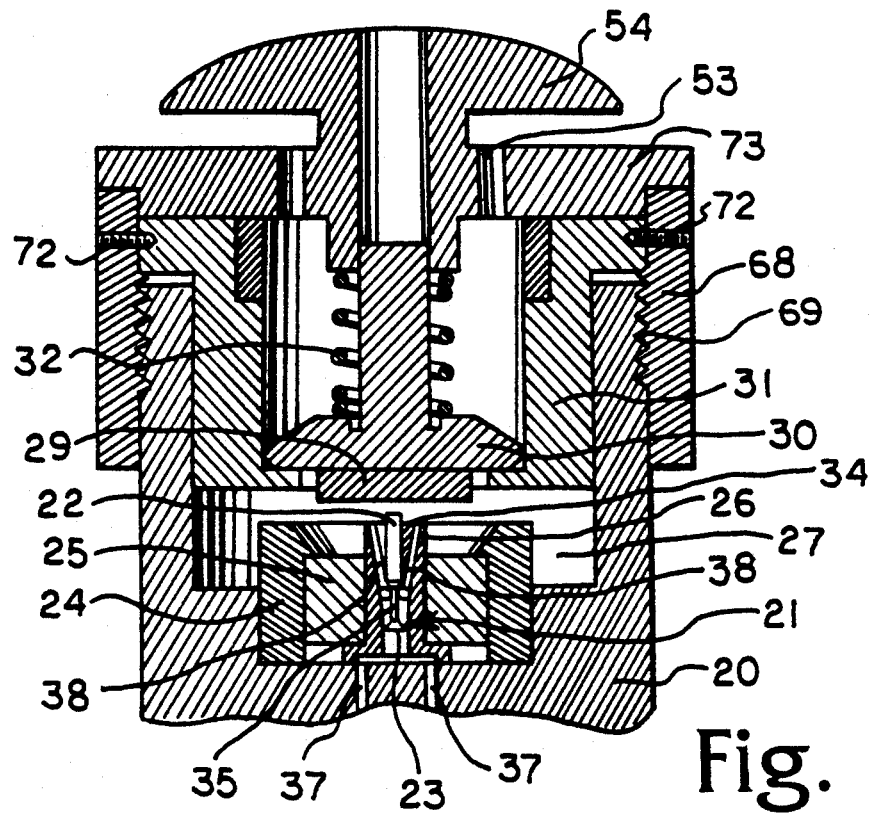
FIG. 5 is a cross-section similar to that of FIG. 1, but of the upper part of the device only, illustrating a modification thereto.

In the arrangement illustrated in FIG. 5, in which reference numerals common with FIG. 2 are used where applicable, the adjustment of the seating member 31 is obtained by an exterior sleeve 70 rotationally connected to the housing 20 via the screw thread 71, and fixedly connected to the seating member 31, via screws 72. Rotation of the sleeve 70 relative to the housing 20 will move the sleeve up or down, depending upon the direction of rotation. The seating member 31, with the cap 73 and deflector 54, will move with the sleeve 70 as a unit. Movement of the seating member 31 will vary the distance, and thus the magnetic attraction, between magnet 25 and the member 29.

Also illustrated in FIG. 5 is a modification to the flow control valve 21. The valve stem 22 preferably has a circular cross-section, reciprocal in a bore 34 in the insert 26, and is relatively closely fitted in the bore 34, but freely slidable therein. The stem 22 has a reduced cross-section 35 just above the head 23, and the head seats against an O-ring 39 positioned in an enlarged portion of the bore 34. The lower end of the insert 26 has an annular recess or chamber 48. Instead of a single passageway 47 in the housing 20 as in FIG. 1, two bores 37 are provided, spaced apart and opening into the recess 36. Further bores 38 extend up from the bore 34 behind the O-ring 39 into the chamber 27. When the valve 21 is opened, flow occurs through the two bores 37, past the head 23 and O-ring 39, and through the bores 38 into chamber 27. The valve stem 22 is guided in the bore 34. The number of bores 38 can vary, for example, three or more. The provision of the two bores 37 is to avoid any possible "jet" action through a single bore or similar passage holding the valve 21 shut.

Figure 6:
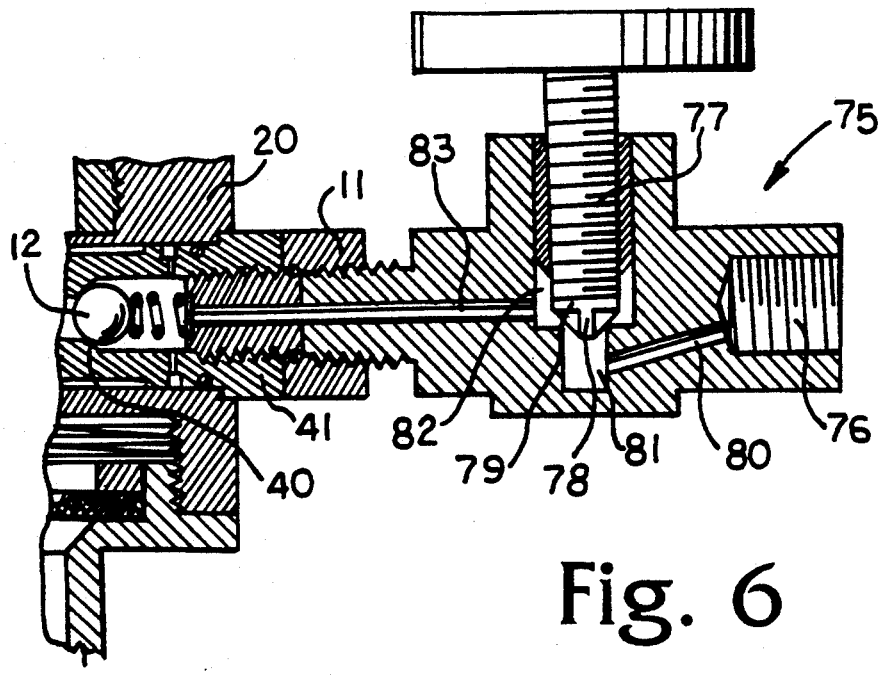
FIG. 6 shows the application of a flow control valve to the main oxygen connection to the device.

For safety and other reasons, the supply of oxygen can be via a control valve which permits a predetermined minimum flow at all times. FIG. 6 illustrates such a valve, indicated generally at 75, connected to the oxygen connection 11, the oxygen supply being connected to the valve 75 at inlet 76. The valve control member 77 has a central bore 78 at its lower end, with a cross-bore 79 spaced above the seating position of the control member 77. Bore 80 connects inlet 76 to a chamber 81 below the valve control member 77. When closed, the control member 77 seats on the upper periphery of the chamber 81, but a minimum flow still occurs through bores 78 and 79 to chamber 82 and thence via a bore 83 to the first valve 12 (see FIGS. 1, 2 and 6). The bores 78 and 79 control the minimum flow. When the valve 12 is opened by operation of the control member 77, increased flow is obtained between the bottom or seat of the control member 77 and the upper periphery of the chamber 81. The maximum flow obtainable can be set by the diameter of the bore 83. The valve 75 controls the minimum flow of oxygen available at all times to the device and also the maximum flow which can be provided to the device. The various valves in the device actually control the flow of oxygen to the user. As an example, the minimum flow can be 40 liters per minute and the maximum flow, 90 liters per minute.

Thus, the invention provides a device or apparatus which can be used for resuscitation or inhalation, as required. There is a safe control of the maximum pressure which can be applied to the lungs, regardless of the pressure of the oxygen supply. The apparatus is operated by hand for resuscitation, or can be set for non-manual control for inhalation. Compared to many forms of apparatus previously used, the present apparatus is very quick to apply and is also very simple. This enables treatment to start very quickly, an important feature where a patient is not breathing or has no pulse. Some of the prior art examples assist in breathing but do not actually "breathe" for the patient, as does the present invention, with both a positive pressure feed and a release of free air pressure between cycles. Prior art examples requiring adjustments to increase and decrease pressures, and with gauges to watch, are not suitable for emergency situations. The present invention provides an apparatus which is light and portable, quickly applied and operates with safe pressures and releases, being simple to use and automatic in function.

It will be understood that various modifications can be made to the above-described embodiments without departing from the spirit or scope of the invention.

I claim:

1. A resuscitation and inhalation device, comprising: a chamber, a gaseous flow control valve to control flow of a gas to said chamber and a first magnetic member associated with said gaseous flow control valve; a movable valve member, acted upon by pressure of gas in said chamber, said movable valve member including a further magnetic member, said movable valve member being biased to act on said gaseous flow control valve to move it to an open position; one of said magnetic members being magnetized, the magnetic field of the magnetized member acting upon the other magnetic member to restrain movement of said movable valve member by said pressure of gas in said chamber; alternate first and second gaseous inlet valves for admitting a first gas under pressure to said gaseous flow control valve; operation of a first of said alternate inlet valves permitting flow only when manually held in an actuated position; operation of a second of said alternate inlet valves permitting continuous flow of gas to said gaseous flow control valve; a mixing chamber; gaseous access means for admitting a second gas to said mixing chamber; and seating means associated with said first alternate inlet valve for closing said gaseous access means on operation of said first inlet valve, whereby on operation of said first inlet valve, said first gas can flow to a connector for flow to a mask, and on operation of said second alternate inlet valve, said first gas is mixed with said second gas in said mixing chamber prior to flowing to said connector and to said mask.

2. A device as claimed in claim 1, the distance between said magnetic members being variable.

3. A device as claimed in claim 2, including a housing, an annular seating member in said housing, said movable valve member being positioned in said annular seating member and seatable on a seat in said seating member; said seating member being movable to vary said distance between said magnetic members.

4. A device as claimed in claim 3, including an external sleeve on said housing and a screw thread between said sleeve and said housing, and means connecting said sleeve to said seating member, whereby rotation of said sleeve on said housing varies said distance between said magnetic members.

5. A device as claimed in claim 3, including an annular magnet in said housing, aligned with and spaced from said movable valve member, said flow control valve being mounted for axial movement in said annular magnet.

6. A device as claimed in claim 1, said first gaseous inlet valve including an operating member, said operating member comprising a button slidable axially in a valve seating member, said first inlet valve comprising a ball valve and said button including an extension for lifting said ball valve off its seating on movement of said button, and biasing means biasing said button to a non-operative position.

7. A device as claimed in claim 1, said second inlet valve comprising a needle-valve.

8. A device as claimed in claim 5, wherein said gaseous flow control valve includes a stem and a head, said movable valve member acting on an end of said stem, said head forming a seating at an end remote from said movable valve member.

9. A device as claimed in claim 8, including an inset in said annular magnet, said stem being movable axially in said inset, and flats on said stem extending the length thereof, for flow of a gas past said stem.

10. A device as claimed in claim 1, said magnetized member being a permanent magnet.

11. A device as claimed in claim 8, including an inset in said annular magnet, said stem being movable axially in said inset, and grooves in said inset extending longitudinally of said stem for flow of a gas past said stem.

* * * * *